US00PP26421P2

(12) United States Plant Patent
Jamieson

(10) Patent No.: US PP26,421 P2
(45) Date of Patent: Feb. 16, 2016

(54) *AGAPANTHUS* PLANT NAMED 'FULL MOON'

(50) Latin Name: *Agapanthus praecox*
Varietal Denomination: Full Moon

(71) Applicant: Richard Jamieson, Kirstenhof (ZA)

(72) Inventor: Richard Jamieson, Kirstenhof (ZA)

(73) Assignee: THE PINK GERANIUM NURSERY, Elsenburg (ZA)

( * ) Notice: Subject to any disclaimer, the term of this patent is extended or adjusted under 35 U.S.C. 154(b) by 10 days.

(21) Appl. No.: 13/999,101

(22) Filed: Jan. 13, 2014

(51) Int. Cl.
*A01H 5/02* (2006.01)

(52) U.S. Cl.
USPC ..... Plt./398

(58) Field of Classification Search
USPC ..... Plt./398
CPC ..... A01H 5/02
See application file for complete search history.

(56) References Cited

PUBLICATIONS http://www.blackdogplants.co.za/gallery01.htm 1 page, 2010.*

* cited by examiner

*Primary Examiner* — Kent L Bell
(74) *Attorney, Agent, or Firm* — Penny J. Aguirre

(57) ABSTRACT

A new cultivar of *Agapanthus* named 'Full Moon', that is characterized by its mid season blooming habit, its full and rounded flower heads of open campanulate flowers, its flowers that are variegated with soft blue-grey margins and dark purple centers (on mid rib vein), and its tall plant height.

2 Drawing Sheets

Botanical classification: *Agapanthus praecox*.
Varietal denomination: 'Full Moon'.

BACKGROUND OF THE INVENTION

The present invention relates to a new and distinct cultivar of *Agapanthus praecox* and will be referred to hereafter by its cultivar name, 'Full Moon'. 'Full Moon' represents a new perennial herb grown for landscape and cut flower use.

The new *Agapanthus* originated as the result of an on going breeding program in Cape Town, Republic of South Africa. The goal of the breeding program was to produce a cultivar of *Agapanthus* that is tall in height with a large round flower form.

'Full Moon' originated as a seedling that arose from seed planted from open pollination of an unnamed plant of *Agapanthus praecox* from the Inventor's breeding program in 2002. The male parent is unknown. The new *Agapanthus* was selected as a single unique plant in December of 2004.

Asexual propagation of the new cultivar was first accomplished by in vitro propagation under the direction of the Inventor in December of 2005 in Cape Town, Republic of South Africa. Asexual propagation by division and tissue culture has determined that the characteristics of this cultivar are stable and are reproduced true to type in successive generations.

SUMMARY OF THE INVENTION

The following traits have been repeatedly observed and represent the characteristics of the new cultivar. The characteristics in combination distinguish 'Full Moon' as a distinct cultivar of *Agapanthus*.

1. 'Full Moon' exhibits a mid season blooming habit.
2. 'Full Moon' exhibits full and rounded flower heads of open campanulate flowers.

3. 'Full Moon' exhibits flowers that are variegated; soft blue-grey margins with dark purple centers (on mid rib vein).
4. 'Full Moon' exhibits a tall plant height.

The female parent differs from 'Full Moon' in having flowers that are non-variegated with less full and less rounded flower heads. 'Full Moon' can be compared to the cultivars 'Benfran' (U.S. Plant Pat. No. 21,705) and 'ATIBlu' (U.S. Plant Pat. No. 14,332). Both are similar to 'Full Moon' in having variegated flowers. 'Benfran' differs from 'Full Moon' in having flowers with darker blue margins and in having a shorter plant height. 'ATIBlu' differs from 'Full Moon' in flowers with tepals that are narrower and in having a shorter plant height.

BRIEF DESCRIPTION OF THE DRAWINGS

The accompanying colored photographs illustrate the overall appearance and distinct characteristics of the new *Agapanthus*. The photographs were taken of a four year-old plant of 'Full Moon' as field grown outdoors in Cape Town, Republic of South Africa.

The photograph in FIG. 1 provides a close-up view of an inflorescence of 'Full Moon'.

Figure 1:
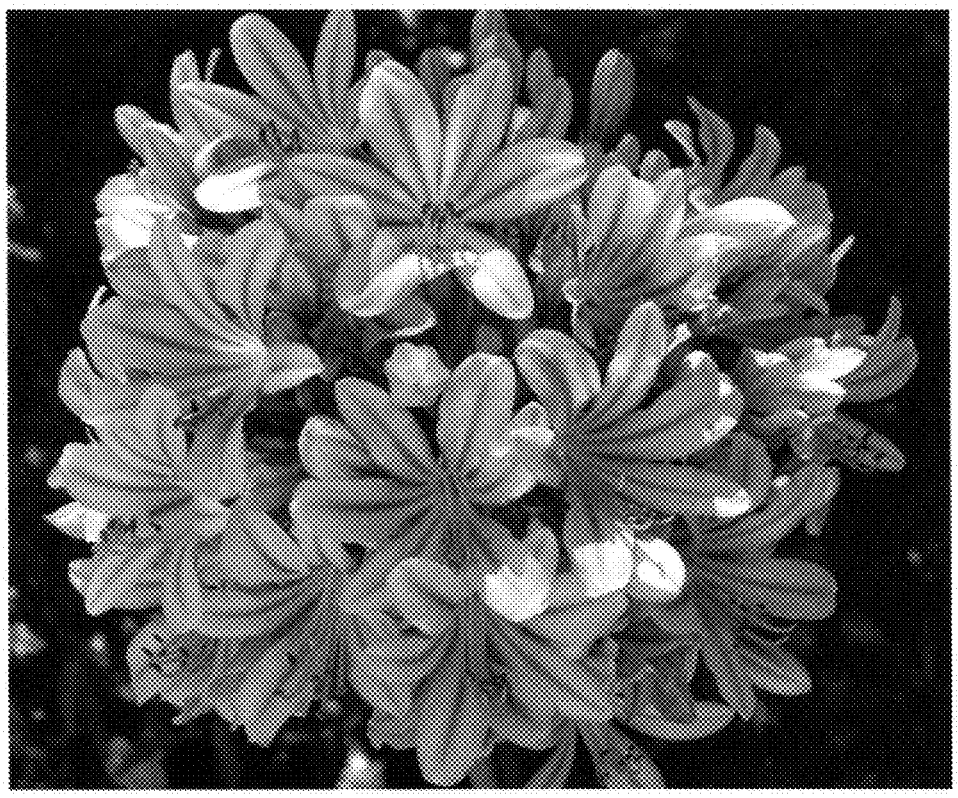
Figure 2:
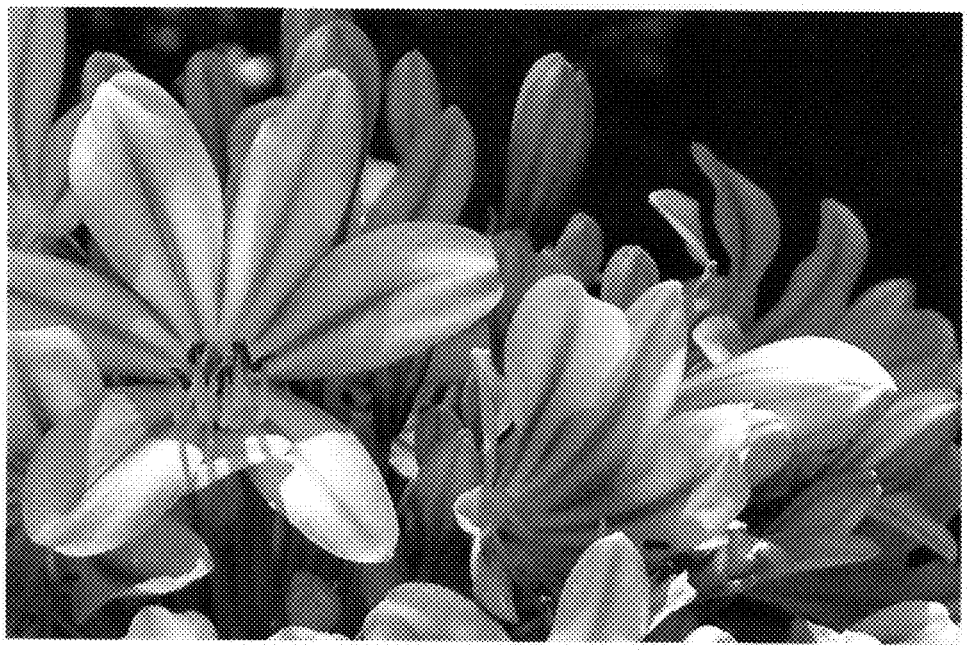

The photograph in FIG. 2 provides a close-up view of the flowers of 'Full Moon'. The colors in the photographs are as close as possible with the photographic and printing technology utilized and color values cited in the detailed botanical description accurately describe the colors of the new *Agapanthus*.

DETAILED BOTANICAL DESCRIPTION

The general observations and descriptions describe plants about two year-old in age as grown outdoors under field conditions in Cape Town, Republic of South Africa. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period.*—4 to 6 weeks in mid summer in Cape Town, Republic of South Africa.

*Plant type*.—Evergreen perennial herb.

*Plant habit*.—Upright stems with cascading foliage.

*Height and spread*.—Reaches a height of about 100 cm in bloom and a spread of about 50 cm.

*Cold hardiness*.—At least to U.S.D.A. Zone 8.

*Diseases and pests*.—No susceptibility or resistance to diseases or pests has been observed.

*Root description*.—Fleshy main roots and fibrous secondary roots.

*Propagation*.—Tissue culture and division.

*Root development*.—A division will root and finish in a 6-inch container in about 90 days at 25° C. with high light intensity.

*Growth rate*.—Moderate.

Foliage description:

*Leaf shape*.—Linear.

*Leaf division*.—Simple.

*Leaf base*.—Cuneate.

*Leaf arrangement.*—2-ranked, in rosette.

*Leaf apex*.—Acute.

*Leaf aspect*.—Emerging leaves erect, then cascade.

*Leaf venation*.—Parallel, color matches leaf coloration.

*Leaf margins*.—Entire.

*Leaf size*.—Average of 64 cm in length and 3.2 cm in width.

*Leaf surface*.—Glabrous, slightly glossy.

*Leaf substance*.—Thick and leathery, moderate to high durability to stress.

*Leaf number*.—Average of 18 per rosette.

*Leaf color*.—Young leaves, upper surface; Green 137C young leaves, lower surface; Green 139D, mature leaves, upper surface; Green 137C and White 157A near base, mature leaves, lower surface; Green 139D and White 157A near base.

*Leaf attachment*.—Sessile to crown.

Flower description:

*Inflorescence type*.—Simple umbel, rounded form.

*Flower fragrance*.—None.

*Flower type*.—Open campanulate.

*Flower number*.—Full flower heads; an average of about 105 flowers per umbel, one umbel per peduncle and one peduncle per rosette.

*Inflorescence size*.—Average of 11 cm in depth and 18 cm in diameter.

*Flower size*.—About 4 cm in depth and 1 cm in width.

*Lastingness of inflorescence*.—About 48 days.

*Longevity as a cut flower*.—About 1 week.

*Flower aspect*.—Held primarily upright from pedicel.

*Peduncle* (*flowering stem*).—Strong, somewhat flattened, held erect, average of 90 cm in length and 1.5 cm in width at distal region and 16 mm in width at proximal region, surface is glabrous, color Yellow-Green 144A.

*Pedicels*.—Strong, average of 3 cm in length and 0.2 mm in width, held erect to outward, color Green 137C, surface is glabrous.

*Flower buds*.—Obovate in shape, average of 4 cm in length and 10 mm in width, color Violet Blue 91A.

*Tepals.*—6, narrow obovate in shape, entire margin, glabrous texture, acute apex, average of 4 cm in length and 10 mm in width, color when young inner surface; Violet Blue 91B with center mid rib Violet Blue 90A, color when young outer surface; Violet Blue 91D with center mid rib Violet Blue 91A, color mature inner surface; Violet Blue 91D with center mid rib Violet Blue 90D, color mature outer surface; Violet Blue 91D with center mid rib Violet Blue 91A.

Reproductive organs:

*Gynoecium.*—1 pistil, average of 1.8 cm in length, stigma is narrow clavate in shape and Violet Blue 97A in color, style is about 1.75 cm in length and Violet Blue 97A in color, ovary is Yellow-Green 15A in color.

*Androecium.*—6 stamens, anthers are dorsified, oblong in shape, average of 2 mm in length, and Brown 199B in color, filament is 2.8 cm in length, pollen is low in quantity and Brown 199B in color.

*Fruit/seed*.—Have not been observed.

It is claimed:

1. A new and distinct cultivar of *Agapanthus* plant named 'Full Moon' as herein illustrated and described.

* * * * *